US009539085B2

(12) United States Patent
Smith et al.

(10) Patent No.: US 9,539,085 B2
(45) Date of Patent: Jan. 10, 2017

(54) DOUBLE-LOOP ENDOBUTTON, OVOID TUNNEL GUIDE, AND METHOD OF ACL RE-CONSTRUCTION USING THE OVOID TUNNEL GUIDE AND THE DOUBLE-LOOP ENDOBUTTON

(71) Applicant: Smith & Nephew, Inc., Memphis, TN (US)

(72) Inventors: Graham Smith, Newburyport, MA (US); Anastasios Dimitrios Georgoulis, Loannina (GR)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 14/331,558

(22) Filed: Jul. 15, 2014

(65) Prior Publication Data

US 2014/0330378 A1 Nov. 6, 2014

Related U.S. Application Data

(62) Division of application No. 13/251,932, filed on Oct. 3, 2011, now Pat. No. 8,784,426.

(51) Int. Cl.
| | |
|---|---|
| *A61B 17/04* | (2006.01) |
| *A61F 2/08* | (2006.01) |
| *A61B 17/17* | (2006.01) |
| *A61B 17/06* | (2006.01) |

(52) U.S. Cl.
CPC ......... *A61F 2/0811* (2013.01); *A61B 17/1714* (2013.01); *A61B 17/1764* (2013.01); *A61B 17/06166* (2013.01); *A61B 2017/0404* (2013.01); *A61F 2002/0852* (2013.01); *A61F 2002/0882* (2013.01); *A61F 2210/0004* (2013.01)

(58) Field of Classification Search
CPC ................... A61F 2/0811; A61F 2/08
See application file for complete search history.

(56) References Cited

U.S. PATENT DOCUMENTS

| | | | |
|---|---|---|---|
| 4,773,910 A * | 9/1988 | Chen | A61F 2/08 623/13.2 |
| 5,152,790 A | 10/1992 | Rosenberg et al. | |
| 7,678,138 B2 | 3/2010 | Fitts et al. | |
| 2007/0162125 A1 * | 7/2007 | LeBeau | A61B 17/0401 623/13.14 |

(Continued)

FOREIGN PATENT DOCUMENTS

| | | |
|---|---|---|
| JP | H08052155 | 2/1996 |
| JP | 2010537746 | 12/2010 |
| RU | 2083179 C1 | 7/1997 |

OTHER PUBLICATIONS

International Search Report, PCT/US2012/058545, Apr. 9, 2013, pp. 7.

(Continued)

*Primary Examiner* — Katrina Stransky
*Assistant Examiner* — Wade P Schutte
(74) *Attorney, Agent, or Firm* — Burns & Levinson LLP; Joseph M. Maraia

(57) ABSTRACT

A graft attachment apparatus including at least two separately formed filament loops, and a fixation member comprising at least one opening configured to receive the at least two separately formed filament loops. The at least two separately formed filament loops are continuous loops.

12 Claims, 4 Drawing Sheets

(56) References Cited

U.S. PATENT DOCUMENTS

2008/0234819 A1    9/2008   Schmieding et al.
2008/0287991 A1   11/2008   Fromm
2009/0018654 A1    1/2009   Schmieding et al.
2010/0249930 A1    9/2010   Myers
2010/0256677 A1   10/2010   Albertorio et al.
2010/0324676 A1   12/2010   Albertorio et al.
2011/0004216 A1    1/2011   Amendola et al.
2012/0059469 A1    3/2012   Myers et al.

OTHER PUBLICATIONS

First Office Action from related Chinese Patent Application No. 201280059466.8 issued Jan. 21, 2016.
Official Action from related Mexican Application No. MX/a/2014/004015 issued Jun. 24, 2016.
Office Action from related Russian Application No. 2014115839114(024822) issued Jun. 9, 2016.
Decision of Rejection from related Japanese Application No. 2013-551405 issued Jul. 25, 2016.
Patent Examination Report from related Australian Application No. 2012318767 issued Aug. 24, 2016.
Second Office Action from related Chinese Application No. 201280059466.8 issued Aug. 25, 2016.
Official Action from related European Application No. 12 806 194.2-1654 issued Jul. 6, 2016.

* cited by examiner

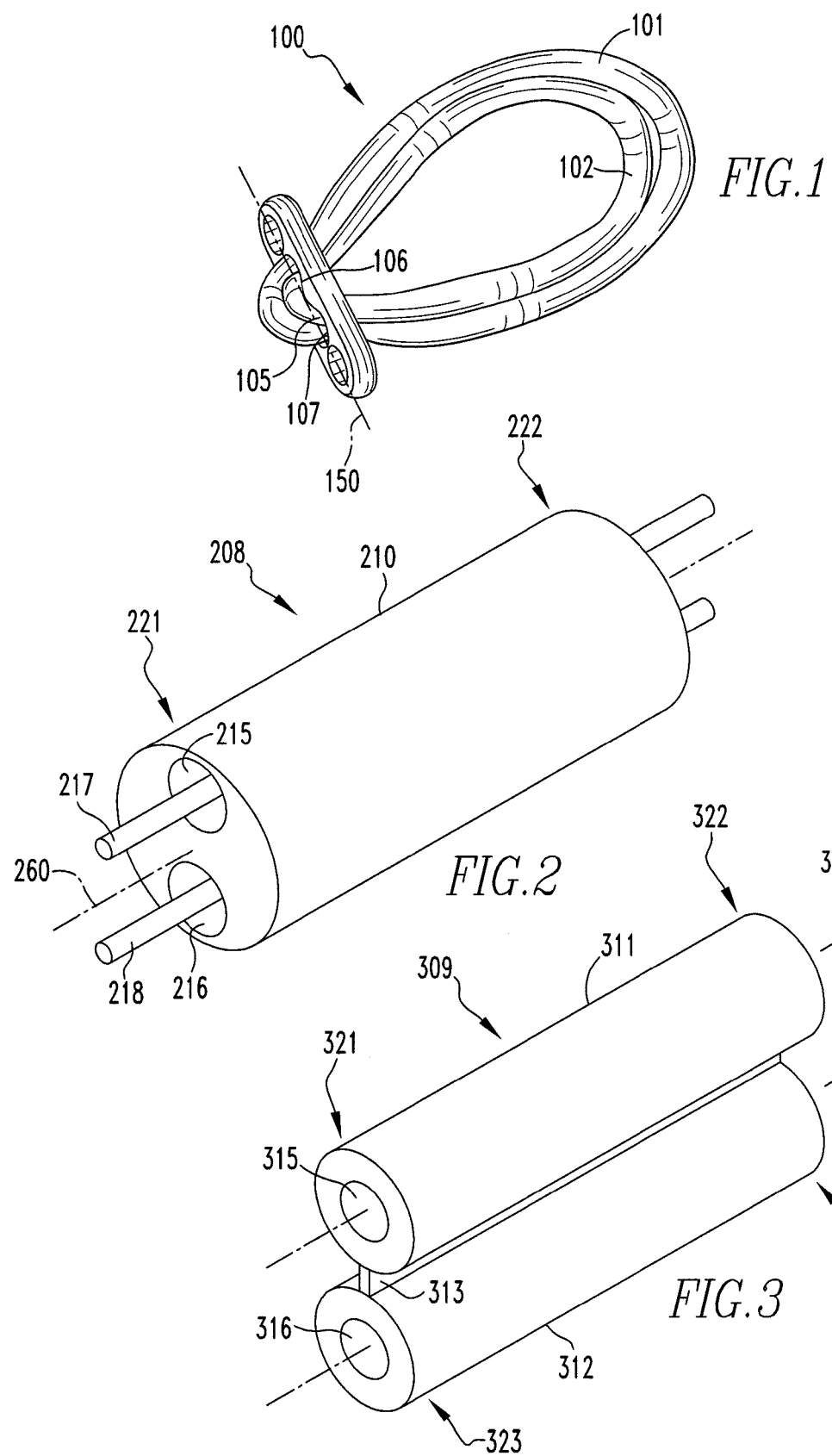

DOUBLE-LOOP ENDOBUTTON, OVOID TUNNEL GUIDE, AND METHOD OF ACL RE-CONSTRUCTION USING THE OVOID TUNNEL GUIDE AND THE DOUBLE-LOOP ENDOBUTTON

This application is a divisional of U.S. application Ser. No. 13/251,932, filed Oct. 3, 2011, now allowed, the teachings and contents of which are incorporated herein by reference.

BACKGROUND OF INVENTION

Anterior cruciate ligament (ACL) re-construction techniques are applied to an increased number of re-construction operations. The ovoid morphology of the native tibial and femoral ACL attachment areas results in the ACL having a continuum of fibers whose length and tension changes differently with knee flexion.

Anteromedial (AM) bundle fibers have been shown to undergo small length changes from full extension to 90 degrees of flexion, whereas posterolateral (PL) bundle fibers demonstrate large changes in length from full extension to 90 degrees of flexion. The anteromedial and posterolateral bundles act synergistically to retrain anterior laxity through the range of knee flexion.

However, many surgeons have been reluctant to adopt double-bundle reconstruction, citing concerns about accurate placement of multiple bone tunnels and femoral condoyle fracture as a result of weakness induced by multiple tunnels.

SUMMARY OF INVENTION

According to one aspect of the present invention, there is provided a graft attachment apparatus including at least two separately formed filament loops, and a fixation member comprising at least one opening configured to receive the at least two separately formed filament loops, in which the at least two separately formed filament loops are coupled to the fixation member, and in which each of the at least two separately formed filament loops are continuous loops.

According to another aspect of the present invention, there is provided a guide apparatus including a body having a proximal end, a distal end, and a longitudinal axis defined therethrough, in which the body includes a first hole and a second hole formed therethrough, in which the first hole is substantially parallel to the second hole, in which each of the first hole and the second hole is configured to receive a guide pin.

According to another aspect of the present invention, there is provided a method of ligament construction, the method including providing a guide configured to guide at least one guide pin into a bone and a fixation device having at least two separately-formed suture loops, in which a first graft and a second graft are each separately coupled to the at least two separately-formed suture loops, forming an oval-shaped socket within a bone, drawing the fixation device through the oval shaped socket, orienting the first graft and the second graft within the oval-shaped socket, and securing the fixation device on an exterior surface of the bone.

BRIEF DESCRIPTION OF DRAWINGS

FIG. 1 is a perspective view of a graft attachment apparatus, in accordance with embodiments disclosed herein.

FIG. 2 is a perspective, schematic view of a guide having a first guide pin and a second guide pin disposed therein, in accordance with embodiments disclosed herein.

FIG. 3 is a perspective, schematic view of a guide, in accordance with embodiments disclosed herein.

DETAILED DESCRIPTION

Figure 4:
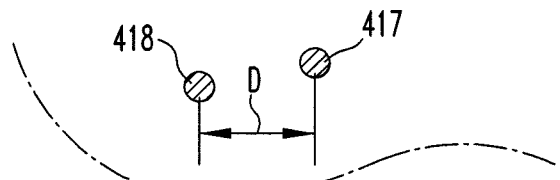
FIG. 4 is a schematic top view of a first guide pin and a second guide pin disposed within a bone, in accordance with embodiments disclosed herein.

The following is directed to various exemplary embodiments of the disclosure. Although one or more of these embodiments may be preferred, the embodiments disclosed should not be interpreted, or otherwise used, as limiting the scope of the disclosure, including the claims. In addition, those having ordinary skill in the art will appreciate that the following description has broad application, and the discussion of any embodiment is meant only to be exemplary of that embodiment, and not intended to suggest that the scope of the disclosure, including the claims, is limited to that embodiment.

Certain terms are used throughout the following description and claims refer to particular features or components. As those having ordinary skill in the art appreciate, different persons may refer to the same feature or component by different names. This document does not intend to distinguish between components or features that differ in name but not function. The figures are not necessarily to scale. Certain features and components herein may be shown exaggerated in scale or in somewhat schematic form and some details of conventional elements may not be shown in interest of clarity and conciseness.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first component is coupled to a second component, that connection may be through a direct connection, or through an indirect connection via other components, devices, and connections. Further, the terms "axial" and "axially" generally mean along or substantially parallel to a central or longitudinal axis, while the terms "radial" and "radially" generally mean perpendicular to a central, longitudinal axis.

As many surgeons have been reluctant to adopt double-bundle re-construction, citing concerns about accurate placement of multiple bone tunnels and femoral condoyle fracture as a result of weakness induced by multiple tunnels, embodiments disclosed herein relate to a graft attachment device that may be coupled with at least two, separate grafts and may be utilized in a single bone tunnel.

Referring to FIG. 1, a graft attachment apparatus 100, according to embodiments disclosed herein, is shown. In one or more embodiments, the graft attachment apparatus 100 may include at least two filament loops 101, 102 and a fixation member 105. In one or more embodiments, the at least two filament loops 101, 102 may be a first filament loop 101 and a second filament loop 102.

In one or more embodiments, the at least two filament loops 101, 102 may be separately formed. As shown, each of the first filament loop 101 and the second filament loop 102 are separately formed loops. In other words, the first filament loop 101 is not connected to, and is not a part of, the second filament loop 102.

Further, in one or more embodiments, the at least two filament loops 101, 102 may be continuous loops. In other words, in one or more embodiments each of the first filament loop 101 and the second filament loop 102 may be continuous loops. As shown in FIG. 1, each of the first filament loop 101 and the second filament loop 102 are continuous loops. In other words, each of the first filament loop 101 and the second filament loop 102 are closed loops that are not tied, or knotted, loops. For example, as shown, neither the first filament loop 101 nor the second filament loop 102 are continuous loops, which are closed loops that are closed without the use of knots.

In one or more embodiments, the at least two filament loops 101, 102 may be at least two separately formed suture loops. In other words, in one or more embodiments, each of the first filament loop 101 and the second filament loop 102 may be separately formed suture loops. However, those having ordinary skill in the art will appreciate that the at least two filament loops 101, 102 may be formed from any material known in the art. For example, in one or more embodiments, each of the first filament loop 101 and the second filament loop 102 may be formed from a continuous loop of polyester, suture, or polyester closure tape.

Further, in one or more embodiments, the at least two separately formed filament loops 101, 102 may be different in length. In other words, a length of the first filament loop 101 may be different from a length of the second filament loop 102. In one or more embodiments, the first filament loop 101 may have a length of 15 mm, and the second filament loop 102 may have a length of 20 mm. However, those having ordinary skill in the art will appreciate that each of the first filament loop 101 and the second filament loop 102 may be of any length. For example, in one or more embodiments, the first filament loop 101 may have a length of 20 mm, and the second filament loop of 15 mm. Further, in one or more embodiments, both the first filament loop 101 and the second filament loop 102 may have equal lengths. Furthermore, in one or more embodiments, each of the first filament loop 101 and the second filament loop 102 may be of any length smaller or larger than 15 mm or 20 mm. In one or more embodiments, the length of the first filament loop 101 and the second filament loop 102 may be dependent on the dimensions, or the type of, graft that may be coupled to each of the first filament loop 101 and the second filament loop 102.

In one or more embodiments, the at least two separately formed loops 101, 102 may be configured to be coupled, or attached, to separate grafts, e.g., anteromedial and posterolateral fiber bundles. However, those having ordinary skill in the art will appreciate that each of the first filament loop 101 and the second filament loop 102 may be configured to be coupled, or attached, to any other grafts known in the art.

As discussed above, in one or more embodiments, the graft attachment apparatus 100 may include the fixation member 105, the fixation member 105 having a longitudinal axis 150 defined therethrough. In one or more embodiments, the fixation member 105 may include at least one opening configured to receive the at least two separately formed suture loops 101, 102. In other words, in one or more embodiments, the fixation member 105 may include at least one opening configured to receive each of the first filament loop 101 and the second filament loop 102. In one or more embodiments, the fixation member 105 may include a single opening, configured to receive both the first filament loop 101 and the second filament loop 102. Alternatively, in one or more embodiments, the fixation member 105 may include a first opening 106 configured to receive the first filament loop 101 and a second opening 107 configured to receive the second filament loop 102. Further, as shown in FIG. 1, in one or more embodiments, the fixation member 105 may include the first opening 106 and the second opening 107, in which both the first opening 106 and the second opening 107 are configured to receive both the first filament loop 101 and the second filament loop 102.

Those having ordinary skill in the art will appreciate that more openings may be formed in, i.e., through, the fixation member 105 than described above. For example, in one or more embodiments, the fixation member 105 may include a third opening (not shown) configured to receive a lead filament (not shown) and a fourth opening (not shown) configured to receive a trailing filament (not shown). In one or more embodiments, the third opening and the fourth opening may be formed on opposite sides of the fixation member 105 with the first opening 106 and the second opening 107 formed between the third opening and the fourth opening. Alternatively, the third opening and the fourth opening may be formed on opposite sides of the fixation member 105 with a single opening configured to receive both the first filament loop 101 and the second filament loop 102, discussed above, formed between the third opening and the fourth opening.

In one or more embodiments, the fixation member 105 may be formed from a biocompatible material. For example, in one or more embodiments, the fixation member 105 may be formed from a biocompatible material such as titanium or acetal. Alternatively, in one or more embodiments, the fixation member 105 may be formed from, or with, a bioabsorbable material such as polylatctic acid or polyglycolic acid.

Furthermore, in one or more embodiments, the fixation member 105 may be elongate, or oblong, in shape. In other words, in one or more embodiments, a length of the fixation member 105 may be larger than a width of the fixation member 105. As shown in FIG. 1, the fixation member 105 is elongate, or oblong, in shape. As such, the fixation member may be received within a tunnel (not shown), in which a diameter of the tunnel is larger than the width of the fixation member 105, but is smaller than the length of the fixation member 105. Accordingly, in one or more embodiments, the fixation member 105 may be disposed within the tunnel, substantially along the longitudinal axis 150 of the fixation member 105. Once the fixation member 105 exits the tunnel, the fixation member 105 may be secured on the of the tunnel, the fixation member 105 may prevent itself from entering back into the tunnel, by being re-oriented such that the longitudinal axis 150 of the fixation member 105 is substantially perpendicular to the tunnel. In other words, because the length of the fixation member 105 is larger than the diameter of the tunnel, the fixation member 105 may prevent itself from entering back into the tunnel by orienting itself such that the length of the fixation member 105 is disposed across the diameter of the tunnel.

According to another aspect, there is provided a guide apparatus. In one or more embodiments, the guide apparatus may be configured to guide a first guide pin and a second guide pin into a body, e.g., disposed, at least partially, within a bone. one or more embodiments, the guide apparatus may include a body having a proximal end, a distal end, and a longitudinal axis defined therethrough. Further, in one or more embodiments, the body may include a first hole and a second hole formed therethrough, in which the first hole is substantially parallel to the second hole, and in which each of the first hole and the second hole is configured to receive a guide pin.

In one or more embodiments, the first hole and the second hole may be separated by a distance of 7 mm. However, those having ordinary skill in the art will appreciate that the first hole and the second hole may be separated by a distance greater than, or less than, 7 mm. For example, in one or more embodiments, the first hole and the second hole may be separated by a distance of 1 mm, 3 mm, 5 mm, 9 mm, 11 mm, or more.

Alternatively, in one or more embodiments, the guide apparatus may include a first body and a second body, in which the first body has a proximal end, a distal end, and a longitudinal axis defined therethrough, and the second body has a proximal end, a distal end, and a longitudinal axis defined therethrough. In one or more embodiments, a first hole may be formed through the first body and a second hole may be formed through the second body, in which each of the first hole and the second hole are configured to receive a guide pin. In other words, in one or more embodiments, the first body may have the first hole formed therethrough, and the second body may have the second hole formed therethrough. In one or more embodiments, the first body may be coupled to the second body.

Further, as discussed above, in one or more embodiments, the first hole and the second hole may be separated by a distance of 7 mm. As such, the first body and the second body may be separated by a distance of substantially 7 mm. However, those having ordinary skill in the art will appreciate that the first hole and the second hole may be separated by a distance greater than, or less than, 7 mm. For example, in one or more embodiments, the first hole and the second hole may be separated by a distance of 1 mm, 3 mm, 5 mm, 9 mm, 11 mm, or more.

Referring to FIG. 2, a schematic, perspective view of a guide 208 having a first guide pin 217 and a second guide pin 218 disposed therein, in accordance with embodiments disclosed herein, is shown. As shown, the guide 208 may include a body 210 having a proximal end 221, a distal end 222, and a longitudinal axis 260 defined therethrough. Further, in one or more embodiments, the guide 208 may include a first hole 215 and a second hole 216 formed therethrough, in which the first hole 215 is substantially parallel to the second hole 216. Further, in one or more embodiments, each of the first hole 215 and the second hole 216 may be configured to receive a guide pin, e.g., the first guide pin 217 and the second guide pin 218, respectively.

In one or more embodiments, each of the first guide pin 217 and the second guide pin 218 may be inserted into, or disposed within, the body 210 of the guide 208 through the first hole 215 and the second hole 216, respectively. In one or more embodiments, the first guide pin 217 may be inserted into the first hole 215 at the proximal end 221 of the body 210 and may exit through the first hole 215 at the distal end 222 of the body 210. Similarly, in one or more embodiments, the second guide pin 218 may be inserted into the second hole 216 at the proximal end 221 of the body 210 and may exit through the second hole 216 at the distal end 222 of the body 210. of the first guide pin 217 and the second guide pin 218 may be received through the body 210 of the guide 208 such that each of the first guide pin 217 and the second guide pin 218 extends in a direction that is substantially parallel to the longitudinal axis 260.

As discussed above, in one or more embodiments, the first hole 215 and the second hole 216 may be separated by a distance of 7 mm. However, those having ordinary skill in the art will appreciate that the first hole 215 and the second hole 216 may be separated by any distance greater than, or less than, 7 mm. For example, in one or more embodiments, the first hole 215 and the second hole 216 may be separated by a distance of 1 mm, 3 mm, 5 mm, 9 mm, 11 mm, or more.

The guide 208 may be formed from any substantially rigid, or substantially flexible, material known in the art. For example, the guide 208 may be formed from any metal, plastic, or polymer known in the art, such as steel or any biocompatible polymer.

Referring to FIG. 3, a schematic, perspective view of a guide 309, in accordance with embodiments disclosed herein, is shown. As shown, the guide 309 may include a first body 311 and a second body 312. In one or more embodiments, the first body 311 may include a proximal end 321, a distal end 322, and a longitudinal axis 361 defined therethrough. Further, in one or more embodiments, the second body 311 may include a proximal end 323, a distal end 324, and a longitudinal axis 362 defined therethrough.

In one or more embodiments, the first body 311 may have a first hole 315 formed therethrough and the second body 312 has a second hole 316 formed therethrough. As discussed above, each of the first body 311 and the second body 312 may be configured to receive a guide pin (not shown), e.g., one of the first guide pin 217 and the second guide pin 218 shown in FIG. 2.

As shown, the first body 311 may be coupled to the second body 312. For example, a connection portion 313 may be coupled between the first body 311 and the second body 312. In one or more embodiments, the first body 311 may be coupled to the second body 312 such that the first hole 315, formed through the first body 311, may be substantially parallel to the second hole 316, formed through the second body 312. Those having ordinary skill in the art will appreciate that the connection portion 313 may not be required for the first body 311 to be coupled to the second body 312. For example, in one or more embodiments, the first body 311 may be directly connected to the second body 312, without the use of a connection portion 313, by means of welding, or otherwise forming the first body 311 and the second body 312 together, known in the art.

In one or more embodiments, a first guide pin (not shown) may be inserted into the first hole 315 at the proximal end 321 of the first body 3 and may exit through the first hole 315 at the distal end 322 of the first body 311. In one or more embodiments, the first guide pin may be received through the first body 311 of the guide 309 such that the first pin extends substantially along the longitudinal axis 361. Similarly, in one or more embodiments, the second guide pin (not shown) may be inserted into the second hole 316 at the proximal end 323 of the body 210 and may exit through the second hole 316 at the distal end 324 of the body 310. In one or more embodiments, the second guide pin may be received through the second body 312 of the guide 309 such that the second guide pin extends substantially along the longitudinal axis 362.

As discussed above, in one or more embodiments, the first hole 315 and the second hole 316 may be separated by a distance of 7 mm. As shown in FIG. 3, the first hole 315 and the second hole 316 are separated by a distance of 6 mm. However, those having ordinary skill in the art will appreciate that the first hole 315 and the second hole 316 may be separated by any distance greater than, or less than, 6 mm or 7 mm. For example, in one or more embodiments, the first hole 315 and the second hole 316 may be separated by a distance of 1 mm, 3 mm, 5 mm, 9 mm, 11 mm, or more.

The guide 309 may be formed from any substantially rigid, or substantially flexible, material known in the art. For example, the guide 309 may be formed from any metal, plastic, or polymer known in the art, such as steel or any biocompatible polymer.

According to another aspect, there is provided a method for ligament construction. The method may include providing a guide configured to guide at least one guide pin into a bone and a fixation device having at least two separately-formed suture loops, in which a first graft and a second graft are each separately coupled to the at least two separately-formed suture loops, forming an oval-shaped socket in a bone, drawing the fixation device through the oval-shaped socket, orienting the first graft and the second graft within the oval-shaped socket, and securing the fixation device on an exterior surface of the bone.

For example, a guide, e.g., the guide 208 of FIG. 2 or the guide 309 of FIG. 3, may be used to guide at least one guide pin, e.g., the first guide pin 217 and the second guide pin 218 of FIG. 2, into a bone. Further, a fixation device may be provided, e.g., the fixation device 100 of FIG. 1, having at least two separately-formed suture loops, the first filament loop 101 and the second filament loop 102 of FIG. 1, in which a first graft and a second graft may each separately coupled to the at least two separately-formed suture loops.

According to one or more aspects, the first graft may be an anteromedial (AM) fiber bundle and the second graft may be a posterolateral (PL) fiber bundle to be used in anterior cruciate ligament (ACL) construction/re-construction. According to one or more aspects, the first graft and the second graft may be different in length. Further, according to one or more aspects, the first graft and the second graft may have other differentiating characteristics. As discussed above, AM bundles may undergo small length changes from full extension to 90 degrees of flexion, whereas PL bundles may demonstrate larger changes in length from full extension to 90 degrees of flexion. Accordingly, according to one or more aspects, each of the at least two separately-formed suture loops of the fixation device may be different in length.

According to one or more aspects, the bone may be a tibia and/or a femur. However, those having ordinary skill in the art will appreciate that the bone may be any bone in a body, and may not be limited to only a tibia and/or a femur. For example, according to one or more aspects, the bone may be a humerus.

According to one or more aspects, forming an oval-shaped socket within a bone may include forming a first tunnel within the bone, forming a second tunnel within the bone, and dilating each of the first tunnel and the second tunnel to form an oval-shaped socket.

For example, a first tunnel and a second tunnel may be formed in a bone by any means known in the art, such as by disposing and removing a first guide pin and a of the first guide pin and the second guide pin, forming a first tunnel and a second tunnel, as will in the art will appreciate that dilating each of the first tunnel and the second tunnel may be accomplished by any bone dilator known in the art.

According to one or more aspects, forming a first tunnel and a second tunnel within the bone may include disposing a first guide pin, at least partially, within the bone, disposing the guide over the first guide pin, in which the first guide pin is received by a first hole of the guide, disposing the second guide pin, at least partially, within the bone, in which the second guide pin is received by a second hole of the guide. According to one or more aspects, the first guide pin may be substantially parallel to the second guide pin.

For example, referring back to FIG. 2, the first guide pin 217 may be disposed within the bone. Further, the guide 208 may be disposed over the first guide pin 217, in which the first guide pin 217 is received by the first hole 215 of the guide 208 near the distal end 222 of the body 210 and may exit the first hole 215 of the guide 208 near the proximal end 221 of the body 208. Furthermore, the second guide pin 218 may be inserted into the second hole 216 of the guide 208 near the proximal end 221 of the body, through the body 210 of the guide 208, may exit the second hole 216 of the body 208 near the distal end 222 of the body 208, and may be disposed, at least partially, within the bone.

As shown in FIG. 2, the first hole 215 may be substantially parallel to the second hole 216. Accordingly, according to one or more aspects, once the first guide pin 217 and the second guide pin 218 are disposed within the bone, the first guide pin 217 may be substantially parallel to the second guide pin 218.

As shown in FIG. 4, a first guide pin 417 may be substantially parallel to a second guide pin 218. Further, as shown, the first guide pin 417 and the second guide pin 418 are separated by a distance D. In one or more embodiments, the distance D may be a distance of 7 mm. As discussed above, those having ordinary skill in the art will appreciate that a first hole (not shown) and a second hole (not shown) may be separated by any distance greater than, or less than, 7 mm. Consequently, according to one or more aspects, the first guide pin 417 and the second guide pin 418, which may also be separated by any distance greater than, or less than, 7 mm. For example, in one or more embodiments, the guide pin 417 and the second hole 418 may be separated by a distance of 1 mm, 3 mm, 5 mm, 9 mm, 11 mm, or more.

Further, according to one or more aspects, forming a first tunnel and a second tunnel within the bone may also include removing the first guide pin from the bone, forming a first tunnel, and removing the second guide pin from the bone, forming the second guide tunnel.

For example, referring back to FIG. 2, according to one or more aspects, removing the first guide pin 217 from the bone may form a first tunnel (not shown) within the bone. The first tunnel may be a space in the bone that was previously occupied by the first guide pin 217. Similarly, according to one or more aspects, removing the second guide pin 218 from the bone may form a second tunnel (not shown) within the bone. The second tunnel may be a space in the bone that was previously occupied by the second guide pin 218. According to one or more aspects, a diameter of the first tunnel may be substantially similar to an outer diameter of the first guide pin 217. Similarly, according to one or more aspects, a diameter of the second tunnel may be substantially similar to an outer diameter of the second guide pin 218. However, those having ordinary skill in the art will appreciate that the diameter of each of the first tunnel and the second tunnel may be larger than the outer diameter of each of the first guide pin 217 and the second guide pin 218.

Alternatively, according to one or more aspects, forming a first tunnel and a second tunnel within the bone may also include drilling the first tunnel over the first guide pin, drilling the second tunnel over the second guide pin, and removing each of the first guide pin and the second guide pin from the bone.

For example, still referring to FIG. 2, once the first guide pin 217 and the second guide pin 218 are disposed within the bone, a cannulated drill (not shown) may be used to drill a first tunnel over the first guide pin 217 and a second tunnel over the second guide pin 218. Further, according to one or more aspects, each of the first guide pin 217 and the second guide pin 218 may be removed from the bone.

Alternatively, as discussed above, once the first guide pin 217 and the second guide pin 218 are disposed within the bone, each of the first guide pin 217 and the second guide pin 218 may be removed from the bone, forming a first tunnel and a second tunnel, respectively. Further, a non-cannulated drill (not shown) may be used to form the first tunnel and the second tunnel within the bone, or enlarge, e.g., widen, the first tunnel and the second tunnel, formed by the first guide pin 217 and the second guide pin 218, respectively, within the bone.

Figure 5:
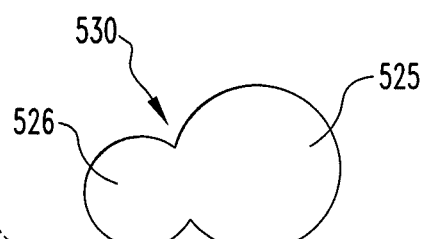
FIG. 5 is a schematic top view of an oval-shaped socket formed in a bone, in accordance with embodiments disclosed herein.

As shown in FIG. 5, an oval-shaped socket 530 is formed from a first tunnel 525 and a second tunnel 526. As discussed above, the first tunnel 525 and the second tunnel 526 may be formed using a first guide pin and a second guide pin (not shown), e.g., the first guide pin 217 and the second guide pin 218 shown in FIG. 2. discussed above, the first tunnel 525 and the second tunnel 526 may be formed by drilling over the first guide pin and the second guide pin, once the first disposed discussed be formed by removing each of the first guide pin and the second guide pin from within the bone, and using a drill, e.g., a non-cannulated drill, to enlarge, e.g., widen, the first tunnel and the second tunnel, formed by the first guide pin and the second guide pin, respectively, within the bone.

According to one or more aspects, a depth of the first tunnel may be different from a depth of the second tunnel. For example, referring to FIG. 6, an oval-shaped socket 630 may have a first tunnel 625, a second tunnel 626, and a longitudinal axis 663 formed therethrough. According to one or more aspects, the first tunnel 625 of the oval-shaped socket 630 may have a different depth than that of a second tunnel 626. For example, the depth of the first tunnel 625 may be 25 mm into a bone, whereas the depth of the second tunnel 626 may be 20 mm into the bone. Those having ordinary skill in the art will appreciate that the depth of each of the first tunnel 625 and the second tunnel 626 may be of any distance less than or greater than 25 mm and 20 mm, and is not limited to 25 mm and 20 mm, respectively. Further, according to one or more aspects, the depth of the first tunnel 625 may be greater than the depth of the second tunnel 626. Alternatively, according to one or more aspects, the depth of the second tunnel 626 may be greater than the depth of the first tunnel 625.

Further, according to one or more aspects, a lead suture may be coupled to the fixation device and the lead suture may be used to draw the fixation device through the oval-shaped socket. In other words, drawing the fixation device through the oval-shaped socket may include drawing the fixation device through the oval-shaped socket with the lead suture.

For example, according to one or more aspects, once a fixation device, e.g., the fixation device 100 shown in FIG. 1, is disposed within an oval-shaped socket, the oval shaped socket 530 shown in FIG. 5, a lead suture coupled to the fixation device may be used to draw, or pull, the fixation device through the oval-shaped socket.

According to one or more aspects, the method may also include orienting the fixation device within the oval-shaped socket, in which orienting the fixation device within the oval-shaped socket may include substantially aligning a longitudinal axis of the fixation device with a longitudinal axis of the oval-shaped socket.

Figure 6:
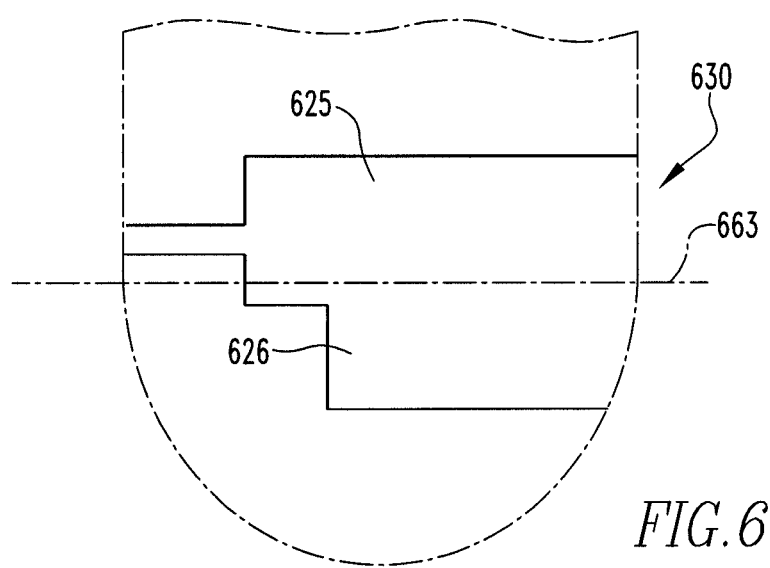
FIG. 6 is a schematic cross-sectional view of an oval-shaped socket formed in a bone, in accordance with embodiments disclosed herein.

For example, according to one or more aspects, once a fixation device, e.g., the fixation device 100 shown in FIG. 1, is disposed within an oval-shaped socket, e.g., the oval-shaped socket 630 shown in FIG. 6, the fixation device may be oriented within the oval-shaped socket such that a longitudinal axis of the fixation device, e.g., the longitudinal axis 150 of the fixation device 100, may be substantially aligned with a longitudinal axis of the oval-shaped socket, e.g., the longitudinal axis 663 of the oval-shaped socket 630. Such an orientation may allow an oval-shaped socket of a minimal diameter, e.g., a diameter that may be only slightly larger than a width of the fixation device. As such, a diameter of the oval-shaped socket may be minimized, while still allowing the fixation device to be drawn, or pulled, through the oval-shaped socket. With the fixation device oriented such that the longitudinal axis of the fixation device is substantially aligned with the longitudinal axis of the oval-shaped socket, the diameter of the oval-shaped socket may only need to be slightly larger than the width of the fixation device in order to allow the fixation device to be received within the oval-shaped socket and be drawn, or pulled, through the oval-shaped socket, by a lead suture, as described above.

According to one or more aspects, orienting the first graft and the second graft within the oval-shaped socket may include turning, twisting, or otherwise re-orienting the fixation device within the oval-shaped socket such that the first graft and the second graft, which may be attached to a first suture loop and a second suture loop of the fixation device, respectively, are aligned as desired. For example, as described above, an AM bundle and a PL bundle may have different characteristics.

As such, it may be advantageous, for recovery purposes, to orient the AM bundle and the PL bundle within the oval-shaped socket in a pre-determined orientation. For example, according to one or more aspects, it may be advantageous to place the AM bundle near an anterior region, and medially, in the tibia, and close to the "over the top" position in the femur. According to one or more aspects, this may be accomplished by turning, twisting, or otherwise re-orienting the fixation device within the oval-shaped socket such that the AM bundle and the PL bundle are aligned in a pre-determined orientation.

According to one or more aspects, securing the fixation device on an exterior surface of the bone may include re-orienting the fixation device such that the longitudinal axis of the fixation device may be substantially perpendicular to the longitudinal axis of the oval-shaped socket.

As discussed above, a diameter of the oval-shaped socket may be minimized, while still allowing the fixation device to be received within, and be drawn through the oval-shaped socket. For example, according to one or more aspects, and as discussed above, the diameter of the oval-shaped socket may only need to be slightly larger than the width of the fixation device in order to allow the fixation device to be drawn, or pulled, through the oval-shaped socket. Subsequently, once the fixation device is drawn through the oval-shaped socket, and exits the oval-shaped socket, the fixation device may be reoriented to prevent the fixation device from being disposed into the oval-shaped socket, retain the fixation device on a surface of the bone.

For example, a fixation device, e.g., the fixation device 100 shown in FIG. 1, the oval shaped socket 630 shown in FIG. 6, and may exit the oval-shaped socket. Further, the fixation device may be re-oriented such that a longitudinal axis of the fixation device, the longitudinal axis 150 of the fixation device 100, is substantially perpendicular to a longitudinal axis of the oval-shaped socket, e.g., the longitudinal axis 663 of the oval-shaped socket 630. As such, this orientation of the fixation device may be such that a length of fixation device, which may be greater than the width of the fixation device, may of the oval-shaped socket on the surface of the bone. Accordingly, as the length of the fixation device may be greater than the width of the fixation device, such an orientation of the fixation device may prevent the fixation device from being disposed into the oval-shape socket, and may retain the fixation device on a surface of the bone.

According to one or more aspects, the oval-shaped socket may include a keyhole-like tunnel. Those having ordinary skill in the art will appreciate that the oval-shaped socket may be an oblong socket, an elliptical socket, or any other shape known in the art. Further, according to one or more aspects, the oval-shaped socket may of any shape that is configured to receive a fixation device, as described above, but may also allow the fixation device to be oriented to prevent the fixation device from being disposed into the oval-shaped socket. Further, those having ordinary skill in the art will appreciate that the oval-shaped socket may be formed completely through a bone, e.g., a tibia and/or a femur. Alternatively, according to one or more aspects, the oval-shaped socket may not necessarily be formed completely through the bone.

Figure 7A:
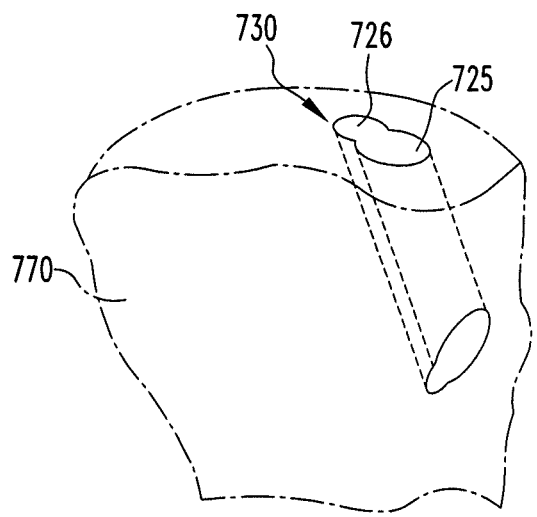
FIGS. 7A-7B are multiple, schematic views of an oval-shaped socket formed in a bone, in accordance with embodiments disclosed herein.
Figure 7B:
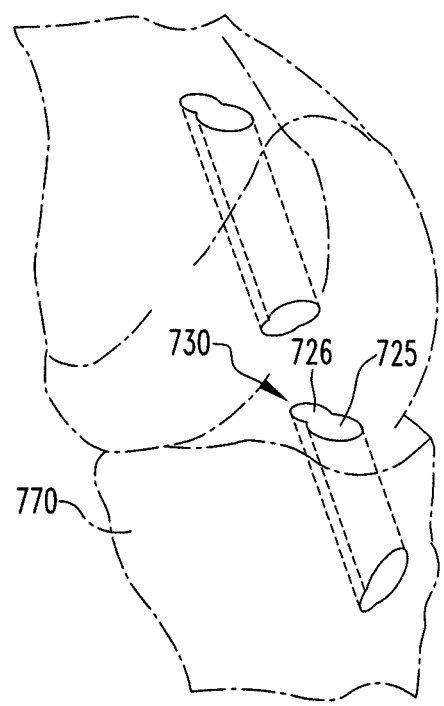

Referring to FIGS. 7A and 7B, an oval-shaped tunnel 730 having a first tunnel 725 and a second tunnel 726 is shown, formed in a femur 770. As discussed above, the oval-shaped socket 730 may be an oblong socket, an elliptical socket, or any other shape known in the art.

Figure 8:
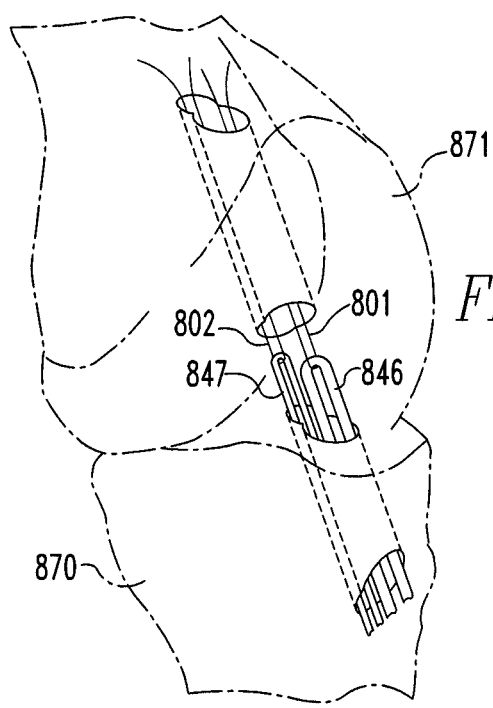
FIG. 8 is a perspective, schematic view of a first graft and a second graft disposed near a femur, in accordance with embodiments disclosed herein.
Figure 9:
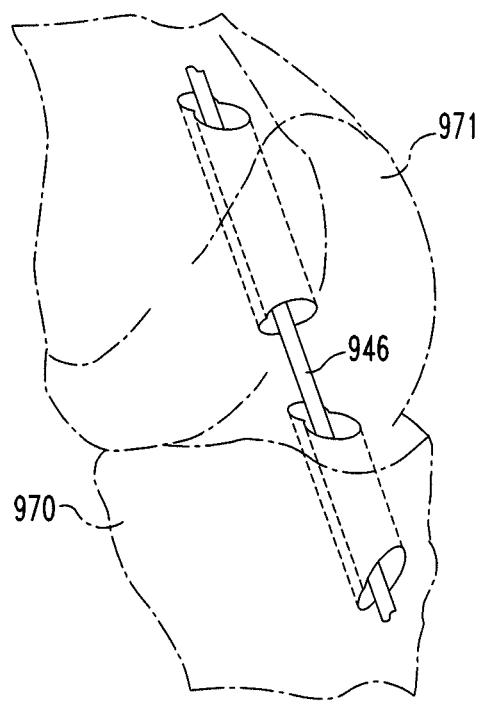
FIG. 9 is a perspective view of a first graft disposed near a femur, in accordance with embodiments disclosed herein.

Referring to FIG. 8, a first graft 846 and a second graft 847 are shown disposed within a body, near a femur 871. As shown, the first graft 846 may be coupled to a first suture loop 80 1 and the second graft 847 may be coupled to a second suture loop 802. As discussed above, the first graft 846 may be an AM bundle and the second graft 847 may be a PL bundle. Further, as discussed above, the AM bundle may be placed near an anterior region, and medially, in the tibia 870, and close to the "over the top" position in the femur 870. Further, referring to FIG. 9, a first graft 946 is shown disposed within a body, near a femur 971 and between the femur and the tibia 970.

Figure 10:
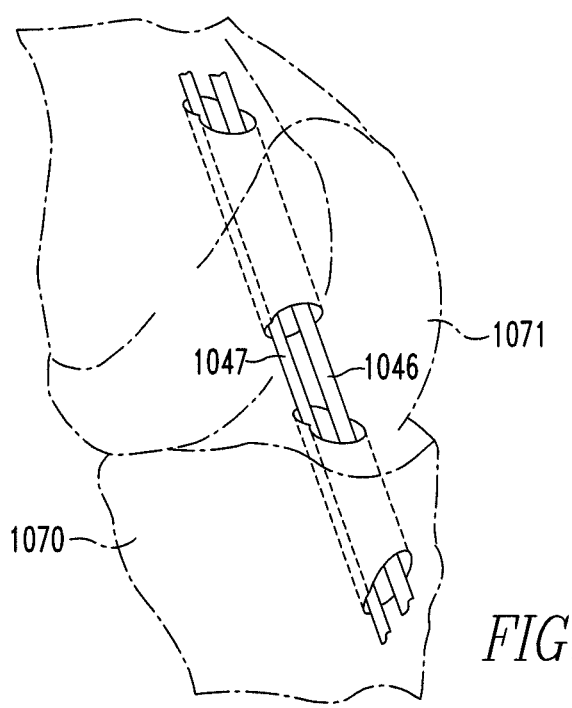
FIG. 10 is a side view of a first graft and a second graft disposed between a femur and a tibia, in accordance with embodiments disclosed herein.

Referring to FIG. 10, a first graft 1046 and a second graft 1047 are shown disposed between a femur 1071 and a tibia 1070. As discussed above, the first graft 1046 may be an AM bundle and the second graft 1047 may be a PL bundle. Further, as discussed above, the AM bundle may be placed near an anterior region, and medially, in the tibia 1070, and close to the "over the top" position in the femur 1071. As also shown in FIGS. 7A, B, FIG. 8 and FIG. 10, the grafts can be oriented so that the first graft 1046 is disposed in the first tunnel 725 (FIG. 7A) or first portion of the oval-shaped tunnel 730 and so the second graft 1047 is disposed in the second tunnel 726 (FIG. 8A) or second portion of the oval-shaped tunnel.

Advantageously, embodiments disclosed herein may provide a graft attachment device that may be coupled with at least two, separate grafts and may be more separate grafts may be coupled to the graft attachment device via the at least two, separately formed, filament loops. As such, multiple-bundle, e.g., double-bundle, ACL re-construction utilizing a single bone tunnel, e.g., a single ovoid femoral and/or tibial tunnel, may be possible, with the fixation of separate antero-medial and posterolateral grafts may be possible. Such type of ACL re-construction may improve the control of knee laxity compared to a standard, anatomic, single-bundle ACL re-construction, without the need for separate bone tunnels.

While embodiments have been described with respect to a limited number of embodiments, those skilled in the art, having benefit of this disclosure, will appreciate that other embodiments can be devised which do not depart from the scope of embodiments disclosed herein. Accordingly, the scope of embodiments disclosed herein should be limited only by the attached claims.

What is claimed is:

1. A graft attachment apparatus comprising:
    at least two separately formed filament loops wherein each of the two separately formed loops are not coupled to one another, each of the at least two separately formed filament loops being continuous loops; and
    a fixation member including:
        a body having a first surface and a second surface opposite the first surface, the first and second surfaces separated by a width of the body, the width of the body remaining constant along a longitudinal axis of the body;
        at least one loop opening extending through the body transverse to the longitudinal axis, the at least one loop opening being configured to receive the at least two separately formed filament loops; and
        a lead filament opening and a trailing filament opening extending through the body transverse to the longitudinal axis, the lead filament opening and the trailing filament opening formed on opposite sides of the fixation member with the at least one loop opening formed between the lead filament opening and the trailing filament opening;
    wherein the at least two separately formed filament loops are coupled to the fixation member such that each of the at least two separately formed filament loops are received within the same one of the at least one loop opening;
    and
    wherein the at least two separately formed filament loops are arranged so that at least one graft is attached or connected to a respective one of the at least two separately formed filament loops.

2. The apparatus of claim 1, wherein the at least two separately formed filament loops comprises at least two separately formed suture loops.

3. The apparatus of claim 1, wherein the fixation device comprises one of a biocompatible or a bio-absorbable material.

4. The apparatus of claim 1, wherein the at least two separately formed filament loops are configured so that each are a different length from each other.

5. The apparatus of claim 1, wherein the fixation member is one of elongate and oblong in shape.

6. The apparatus of claim 1, wherein the apparatus is configured so as to be received in a bone having at least a first and a second tunnel formed therein and conjoined with each other; and
    wherein the at least two separately formed filament loops and the fixation device are configured so that one filament loop and its respective graft can be manipulated so that it is disposed in the first tunnel and so that another filament loop can be manipulated so as to be disposed in the second tunnel.

7. The apparatus of claim 6, wherein the at least two separately formed filament loops are configured so that each are a different length from each other.

8. The apparatus of claim 6, wherein a line is coupled to the fixation member such that when the line is pulled it draws the fixation member through at least one of the tunnels.

9. The apparatus of claim 6, wherein the at least two separately formed filament loops and the respective grafts are configured and arranged so as to be movable within the first and second tunnels so that the at least two separately formed filament loops and the respective grafts can be arranged so as to be in a desired alignment.

10. The apparatus of claim 9, wherein the apparatus is useable in an anterior cruciate ligament construction/reconstruction technique, one of the at least two separately formed filament loops and the respective graft are arranged to form an anteromedial (AM) fiber bundle, another of the at least two separately formed filament loops and the respective graft are arranged to form a posterolateral (PL) fiber bundle, and the combination of one of the at least two filament loops and the respective graft are manipulated so that the combination is disposed in the first tunnel and the combination of the another filament loop and respective graft are be manipulated so as to be disposed in the second tunnel.

11. The apparatus of claim 1, wherein the fixation member is at least one dimension that is larger than an opening in the bone formed by the first and second tunnels.

12. The apparatus of claim 1, wherein the at least two separately formed filament loops are configured and arranged so at least one of the separately formed loops is such that at least two grafts are separately coupled to the at least one of the separately formed loops.

\* \* \* \* \*